United States Patent
Hegland et al.

(10) Patent No.: US 9,889,252 B2
(45) Date of Patent: Feb. 13, 2018

(54) INFUSION DEVICE ASSEMBLY

(71) Applicant: MEDTRONIC, INC., Minneapolis, MN (US)

(72) Inventors: Michael T. Hegland, Mounds View, MN (US); Dale F. Seeley, Spring Park, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 604 days.

(21) Appl. No.: 14/303,793

(22) Filed: Jun. 13, 2014

(65) Prior Publication Data
US 2014/0371675 A1 Dec. 18, 2014

Related U.S. Application Data

(60) Provisional application No. 61/834,986, filed on Jun. 14, 2013.

(51) Int. Cl.
*A61M 5/14* (2006.01)
*A61M 5/142* (2006.01)

(52) U.S. Cl.
CPC ......... *A61M 5/14248* (2013.01); *A61M 2005/14268* (2013.01); *A61M 2205/58* (2013.01); *A61M 2209/04* (2013.01)

(58) Field of Classification Search
CPC ............ A61M 5/1456; A61M 5/14244; A61M 5/1413; A61M 2005/14268; A61M 5/14566
See application file for complete search history.

(56) References Cited

U.S. PATENT DOCUMENTS

| | | | |
|---|---|---|---|
| 4,378,015 A * | 3/1983 | Wardlaw | 604/137 |
| 4,562,751 A | 1/1986 | Nason | |
| 4,678,408 A | 7/1987 | Nason | |
| 4,685,903 A | 8/1987 | Cable | |
| 5,080,653 A | 1/1992 | Voss | |
| 5,097,122 A | 3/1992 | Colman | |
| 6,056,718 A * | 5/2000 | Funderburk et al. | 604/93.01 |
| 6,551,276 B1 | 4/2003 | Mann | |
| 6,984,222 B1 * | 1/2006 | Hitchins et al. | 604/218 |
| 8,372,039 B2 * | 2/2013 | Mernoe et al. | 604/131 |
| 8,500,773 B2 * | 8/2013 | Nardone et al. | 606/200 |
| 9,192,717 B2 * | 11/2015 | Cote et al. | |
| 2001/0011163 A1 * | 8/2001 | Nolan et al. | 604/154 |
| 2002/0040208 A1 * | 4/2002 | Flaherty et al. | 604/288.01 |
| 2002/0161332 A1 * | 10/2002 | Ramey | 604/164.07 |
| 2003/0060781 A1 * | 3/2003 | Mogensen et al. | 604/257 |
| 2003/0158520 A1 * | 8/2003 | Safabash et al. | 604/116 |
| 2004/0002682 A1 * | 1/2004 | Kovelman et al. | 604/136 |
| 2004/0204673 A1 * | 10/2004 | Flaherty | 604/65 |
| 2006/0041224 A1 * | 2/2006 | Jensen | 604/93.01 |
| 2007/0049870 A1 * | 3/2007 | Gray et al. | 604/158 |
| 2007/0167912 A1 * | 7/2007 | Causey et al. | 604/131 |
| 2008/0154205 A1 * | 6/2008 | Wojcik | 604/164.01 |

(Continued)

*Primary Examiner* — Scott Medway
(74) *Attorney, Agent, or Firm* — Mueting, Raasch & Gebhardt, P.A.

(57) ABSTRACT

Multicomponent infusion device assemblies include locking and unlocking mechanisms that allow for locking and unlocking of components via actions capable of being carried out by at least some patients suffering from movement disorders. Tools or disengagement components may be used to unlock or disengage the components.

8 Claims, 16 Drawing Sheets

(56) References Cited

U.S. PATENT DOCUMENTS

2009/0143763 A1\* 6/2009 Wyss et al. .................. 604/506
2009/0281497 A1   11/2009 Kamen
2011/0218516 A1\* 9/2011 Grigorov ...................... 604/500
2012/0150123 A1\* 6/2012 Lawrence et al. ............ 604/180
2014/0261758 A1\* 9/2014 Wlodarczyk et al. ... 137/315.01

\* cited by examiner

INFUSION DEVICE ASSEMBLY

RELATED APPLICATION

This application claims the benefit of U.S. Provisional Patent Application No. 61/834,986, filed Jun. 14, 2013, which application is hereby incorporated herein by reference in its entirety to the extent that it does not conflict with the present disclosure.

TECHNICAL FIELD

The present disclosure relates generally to wearable infusion devices, such as patch pumps, for transcutaneous or transdermal delivery of therapeutic agents to patients; more particularly to modular external infusion device assemblies having a reusable portion and a disposable portion.

BACKGROUND

Wearable external infusion devices and systems are relatively well known in the medical arts for use in delivering or dispensing a prescribed medication to a patient. In one form, such devices comprise a relatively compact pump housing adapted to receive a syringe or reservoir carrying a prescribed medication for administration to the patient through infusion tubing and an associated catheter or infusion set.

Modular wearable external devices have been described where a portion housing a pumping mechanism is reusable and a portion housing a reservoir is disposable. The portion housing the reservoir is releasably securable to the portion housing the reservoir. The portion housing the reservoir may be swapped out for a new portion housing a reservoir filled with fresh therapeutic agent when the reservoir is empty or becomes nearly empty, when the therapeutic agent in the housing has exceeded its shelf life, etc. Examples of multi-component wearable infusion pump assemblies having disposable and reusable components are described in, for example, U.S. Patent Application Publication No. 2009/0281497, published on Nov. 12, 2009 and entitled WEARABLE PUMP ASSEMBLY, which patent application is hereby incorporated herein by reference in its entirety to the extent that it does not conflict with the disclosure presented herein.

In some forms, modular external infusion devices having releasably securable components require a good deal of dexterity to lock and unlock the components. For certain patient populations, such as those having diabetes, the locking mechanism and actions required to lock and unlock the components (e.g., to swap out an older component housing a reservoir with a newer component housing a reservoir with fresh therapeutic agent) present little challenge. However, for other patient populations, including patients that suffer from movement disorders such as Parkinson's disease, the locking and unlocking mechanisms and actions required to lock and unlock components can present significant challenges.

SUMMARY

In various embodiments described herein, multicomponent infusion device assemblies, among other things, have locking and unlocking mechanisms that may be activated by relatively simple actions. In some embodiments, such actions are capable of being carried out by at least some patients suffering from movement disorders.

In various embodiments, the multicomponent infusion device assemblies described herein, among other things, have unidirectional locking mechanisms and unidirectional unlocking mechanisms.

In various embodiments, a wearable infusion device assembly includes a first component forming a first portion of a housing of the assembly and comprising an inwardly deflectable element. The wearable infusion device assembly also includes a second component forming a second portion of the housing of the assembly and comprising an engagement element comprising (i) a tapered portion configured to cause the inwardly deflectable element of the first component to deflect inwardly as the second component is advanced about the first component and (ii) a shoulder distal to the tapered portion. The inwardly deflectable element of the first component is configured to deflect outwardly after the shoulder passes the inwardly deflectable element as the second component is advanced about the first component. The shoulder and the inwardly deflectable element are configured to cooperate to prevent withdrawal of the second component over the first component after the inwardly deflectable element of the first component has deflected outwardly after the shoulder has passed the inwardly deflectable element as the second component is advanced about the first component. In some embodiments, the assembly includes a disengagement component configured to advance over the second component towards the first component, the disengagement component having a disengagement element comprising a tapered portion configured to cause the inwardly deflectable element of the first component to deflect inwardly as the disengagement component is advanced about the first component. The tapered portion of the disengagement element is configured to sufficiently inwardly deflect the inwardly deflecting element to allow the second component to be withdrawn over the first component. In some embodiments, a system includes the wearable infusion device assembly and a disengagement tool configured to advance over the second component towards the first component, the disengagement tool having a disengagement element comprising a tapered portion configured to cause the inwardly deflectable element of the first component to deflect inwardly as the disengagement tool is advanced about the first component. The tapered portion of the disengagement tool is configured to sufficiently inwardly deflect the inwardly deflecting element to allow the second component to be withdrawn over the first component.

The schematic drawings in are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like.

Any direction referred to herein, such as "top," "bottom," "left," "right," "upper," "lower," "above," below," and other directions and orientations are described herein for clarity in reference to the figures and are not to be limiting of an actual device or system or use of the device or system. Many of the devices, articles or systems described herein may be used in a number of directions and orientations.

Figure 1A:
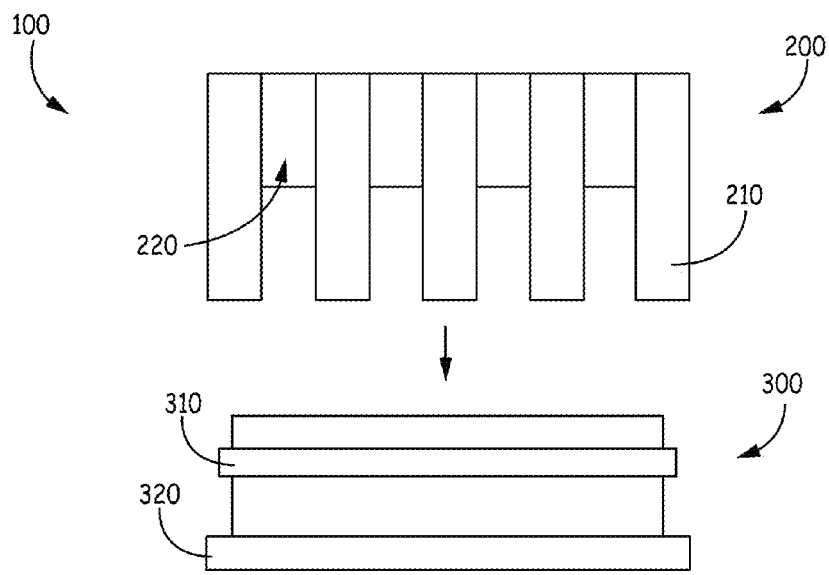
FIGS. 1A-B are schematic drawings of side views of an embodiment of a multicomponent infusion device assembly in an unlocked or disengaged (1A) and locked or engaged (1B) configurations.
Figure 1B:
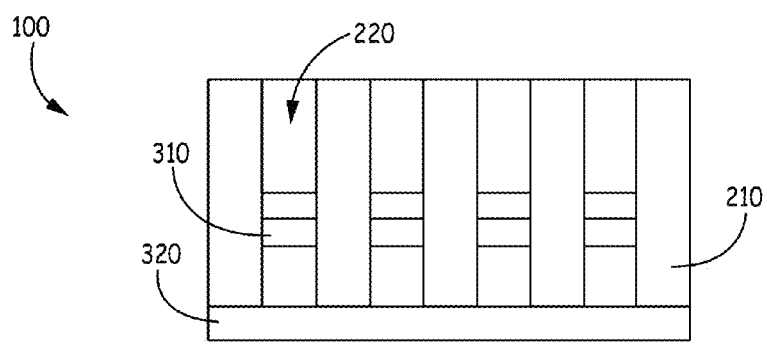

Referring now to FIGS. 1A-B, schematic side views of a multicomponent infusion device assembly 100 are shown. The assembly 100 includes a second component 200 and a first component 300 that is releasably securable relative to the second component 200. In FIG. 1A the components 200, 300 are separated, and in FIG. 1B the components are secured or locked relative to each other, which occurs by advancing the second component 200 over the first component 300. Each of the first 300 and second components 200 form a portion of the housing of the assembly 100 when assembled or secured relative to each other.

The depicted first component 300 includes an inwardly deflectable element 310 to assist in securing the first component 300 relative to the second component 200 as, for example, described in more detail below. The depicted first component 300 also includes a bottom flange 320.

The depicted second component 200 includes a plurality of engagement elements 210 that cooperate with the inwardly deflecting element 310 of the second component to secure the first component relative to the second component as will be described in more detail below. The depicted second component 300 also includes channels 220 for receiving disengagement elements of a disengagement tool or component as will be described in more detail below.

The first component 300 or the second component 200 may include a reservoir for housing a therapeutic agent. The first component 300 or the second component 200 may include a pumping mechanism for delivering the therapeutic agent within the reservoir to the patient. The component comprising the pumping mechanism may also include electronics for operating or controlling the pumping mechanism.

Either of the first component 300 or the second component 200 may be reusable or disposable. In some embodiments, the component that comprises the reservoir is disposable. In some embodiments, the component that comprises the pumping mechanism is reusable.

Figure 2A:
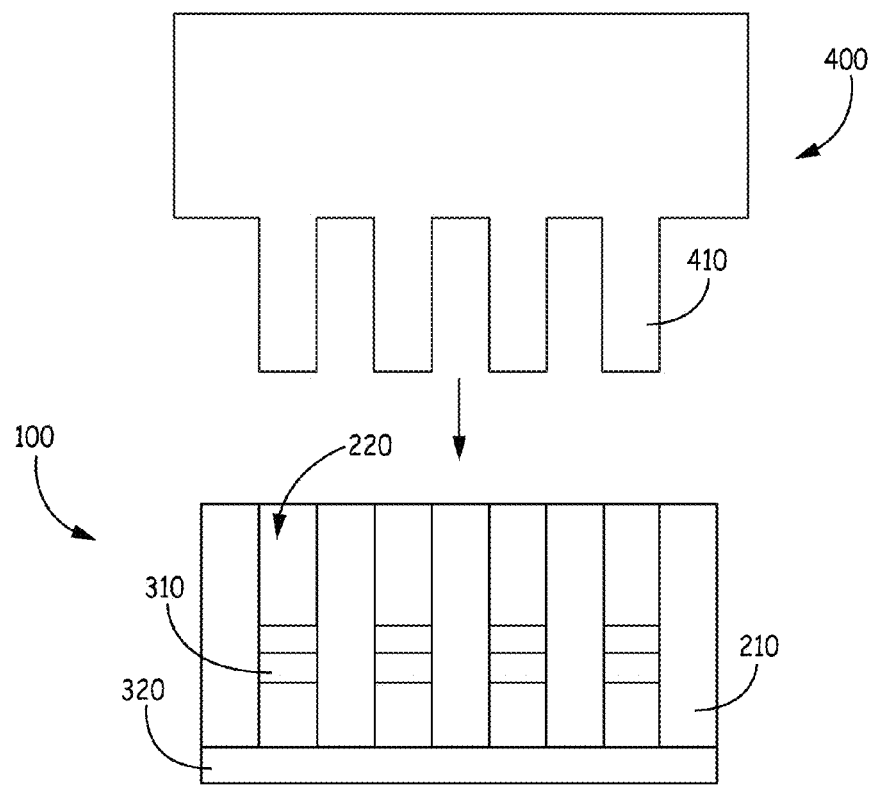
FIGS. 2A-C are schematic drawings of side views of an embodiment of a system including a multicomponent infusion device assembly and a tool for unlocking or disengaging components of the infusion device assembly.
Figure 2B:
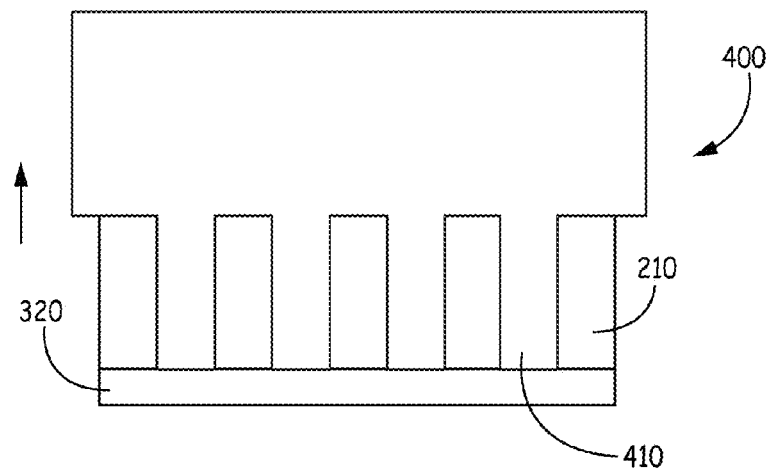
Figure 2C:
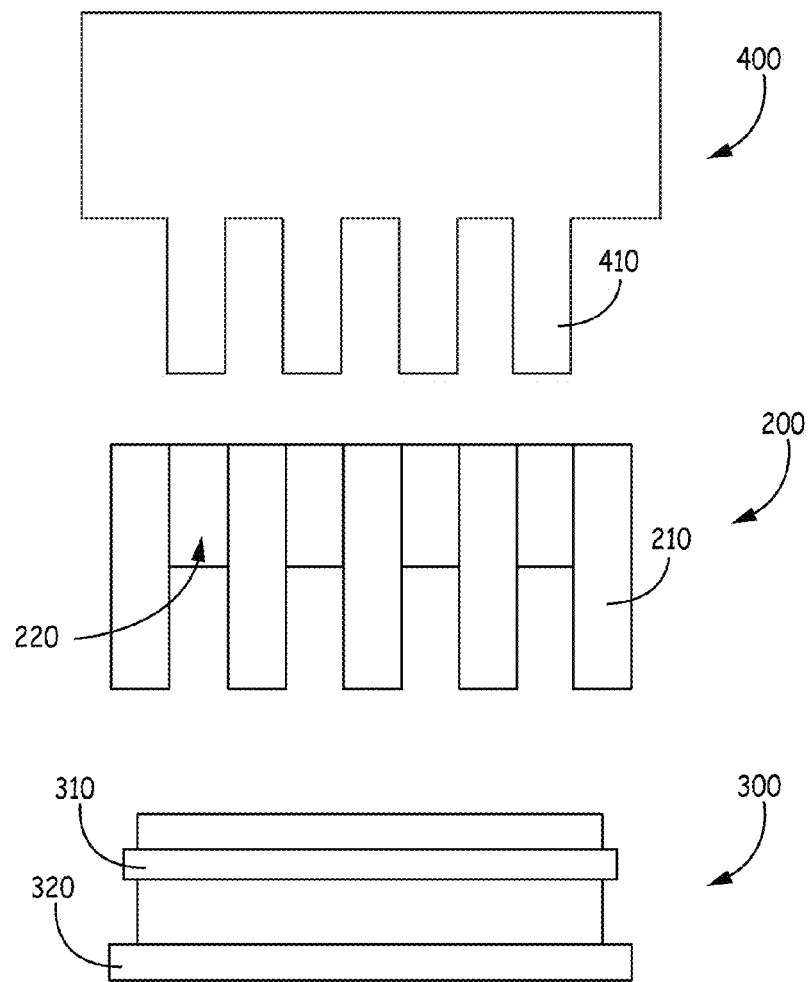

Referring now to FIGS. 2A-C, schematic drawings of side views are shown of an embodiment of a system including a multicomponent infusion device assembly 100 and a tool 400 for unlocking or disengaging components 200, 300 of the infusion device assembly 100. The depicted tool 400 includes a plurality of disengagement members 410 extending from a generally tubular body 420.

In FIG. 2A, the components 200, 300 of the infusion device assembly 100 are locked together. The disengagement tool 400 is advanced over the second component such that the disengagement elements 410 are received by the channels 220 until the disengagement elements 410 contact the flange 310 of the first component. The disengagement elements 410 disengage the inwardly deflecting element 310 of the first component from the engagement elements 210 of the second component such that the first component 300 may be withdrawn over the second component 200 (FIG. 2C).

Figure 3:
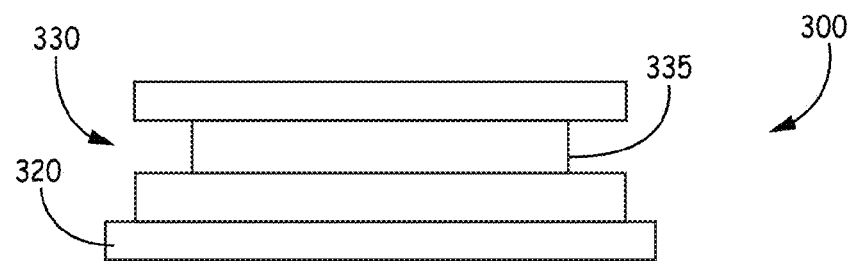
FIG. 3 is a schematic drawing of a side view of an embodiment of a component of a multicomponent infusion device assembly.
Figure 4:
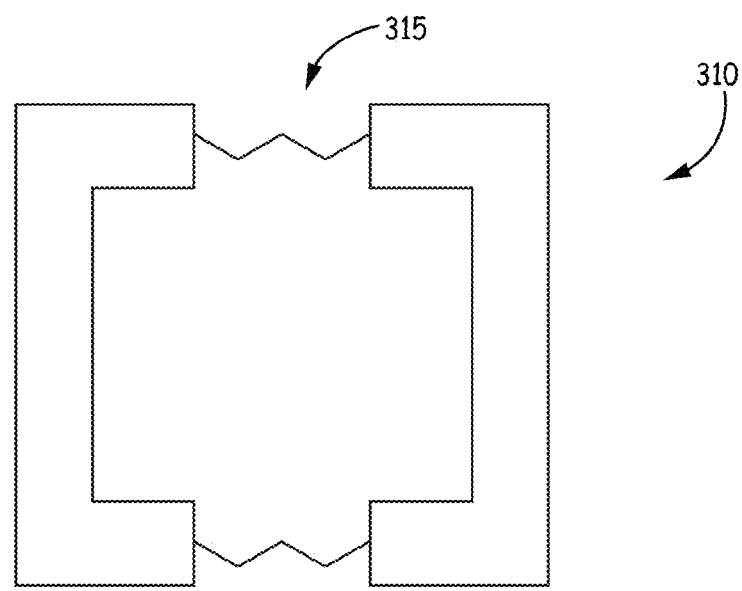
FIG. 4 is a schematic drawing of a top view of an embodiment of an inwardly deflecting element.
Figure 5:
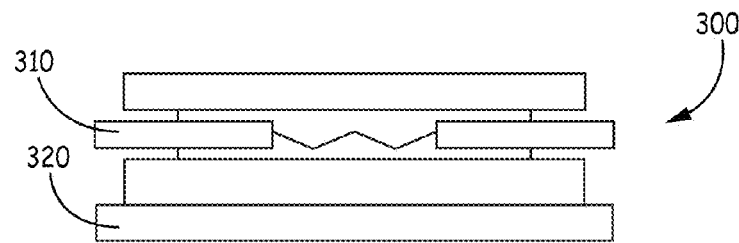
FIG. 5 is a schematic side view of an embodiment of a component as shown in FIG. 3 including the inwardly deflecting element as shown in FIG. 4.

Referring now to FIG. 3-5, a schematic side view of an embodiment of a first component 300 is shown (FIG. 3), a schematic top view of an embodiment of an inwardly deflectable element 310 (FIG. 4) is shown, and a schematic side view is shown of an embodiment of a component 300 as shown in FIG. 3 including the inwardly deflecting element 310 as shown in FIG. 4. The first component 300 includes a recess 330 configured to receive the inwardly deflecting element 310. The recess 330 includes an interior sidewall 335. The inwardly deflectable element 310 includes one or more biasing elements 315 that bias the inwardly deflectable element 310 towards an outwardly extending configuration.

Figures 6, 7:
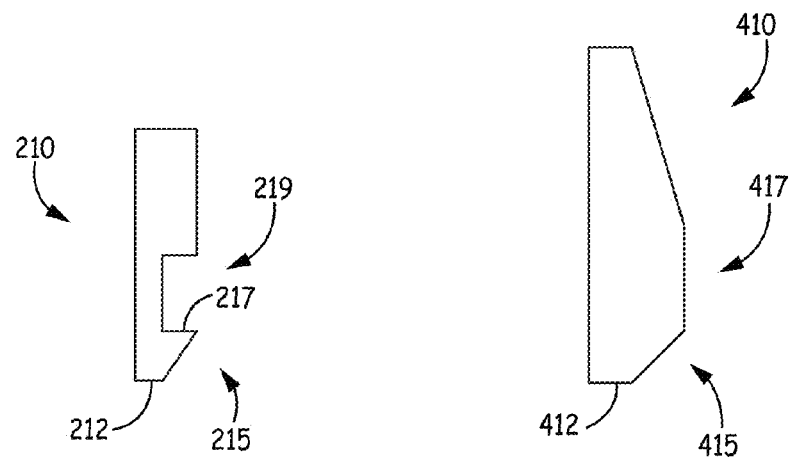
FIG. 6 is a schematic side view of an embodiment of an engagement element of a component (such as the upper component shown in FIG. 1A) of a multicomponent infusion device assembly.
FIG. 7 is a schematic side view of an embodiment of a disengagement element of a disengagement component or tool (such as shown in FIGS. 2A-C).

Referring now to FIG. 6, a schematic side view of an embodiment of an engagement element 210 (such as an engagement element of the second component as shown in FIG. 1A) is shown. The engagement element 310 has a distal end 212 and a tapered portion 215 that tapers outwardly from the distal end 212. Proximal to the tapered portion 215, the engagement element 210 has a shoulder 217 that forms a portion of a groove 219 configured to receive an inwardly deflecting element of a first component (not shown in FIG. 6).

Referring now to FIG. 7, a schematic side view of an embodiment of a disengagement element 410 (such as a disengagement element of a disengagement tool as shown in FIG. 2A) is shown. The disengagement element 410 has a distal end 412 and a tapered portion 415 that extends outwardly from the distal end. Proximal to the tapered portion 415, the disengagement element 410 includes a retention portion 417 configured to retain an inwardly deflecting element (not shown in FIG. 7) of a first component in an inwardly deflected position.

Figure 8A:
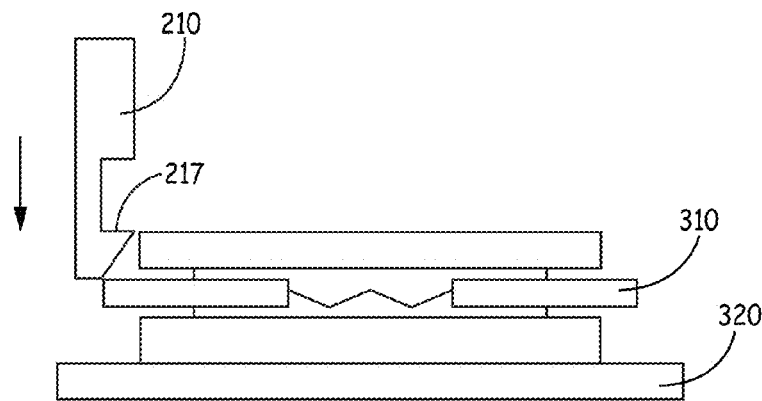
FIGS. 8A-C are schematic side views showing interaction of an embodiment of an engagement element of one component of a multicomponent infusion device assembly with an embodiment of an inwardly deflectable element of another component of the infusion device assembly to secure the two components relative to one another.
Figure 8B:
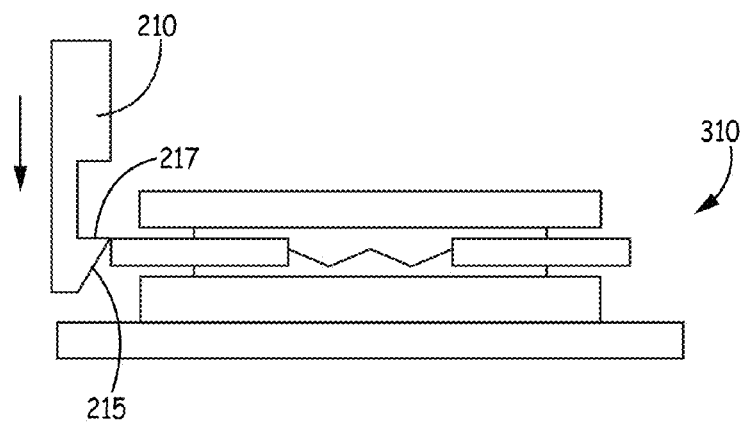
Figure 8C:
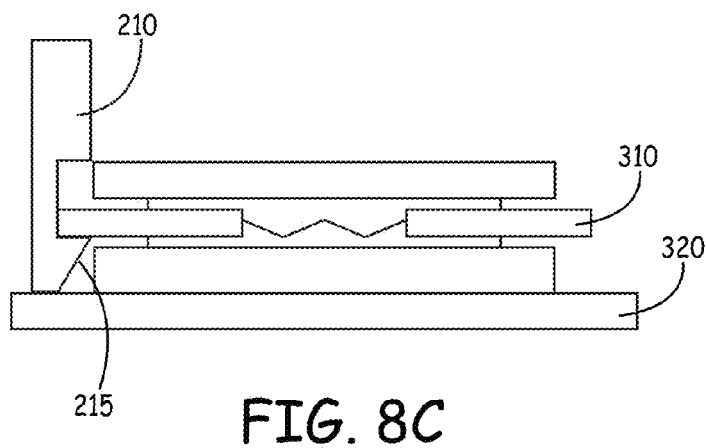

Referring now to FIGS. 8A-C, locking interaction of a first component with a second component are shown. For purposes of clarity, interaction of only one engagement element 210 of a second component (e.g., second component 200 shown in FIG. 1A) with a first component 300 is shown. The second component (as indicated by the engagement element 210) is shown advancing over the first component 300 from FIG. 8A to FIG. 8C. As shown between FIG. 8A and FIG. 8B, the tapered portion 215 of the engagement element 210 engages the inwardly deflecting element 310 as the second component is advanced over the first component 300, causing the inwardly deflecting element 310 to deflect inwardly. Continued advancement of the second portion over the first portion 300 until the shoulder 217 of the engagement element 210 has passed the inwardly deflecting element 310 allows the inwardly deflecting element 310 to deflect outwardly towards its biased or natural state. Once the inwardly deflecting element 310 has deflected outwardly, withdrawal of the second component over the first component is prevented by interaction of the inwardly deflecting element 310 and the shoulder of the engagement element 210. As shown in FIG. 8C, further advancement of the second component over the first component 310 is prevented by interaction of the engagement element 210 and the bottom flange 320 of the first component 300.

Figure 9A:
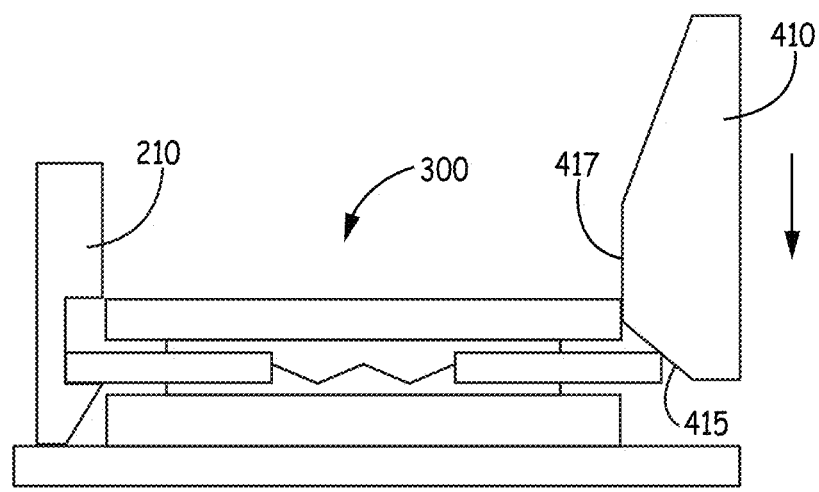
FIGS. 9A-B are schematic side views showing interaction of an embodiment of an disengagement element of a disengagement component or tool with an embodiment of an inwardly deflectable element of a component of an infusion device assembly to allow disengagement of the component the infusion device assembly from another component.
Figure 9B:
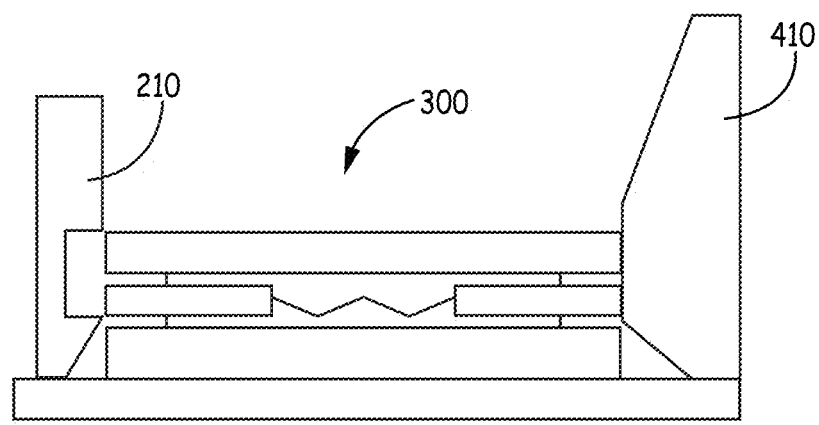

Referring now to FIGS. 9A-B, unlocking first and second components of an infusion device assembly with an unlocking tool is shown. For purposes of clarity, interaction of only one engagement element 210 of a second component (e.g., second component 200 shown in FIG. 1A) with a first component 300 is shown, and only one disengagement member 410 of a tool (such as disengagement tool 400 as shown in FIG. 2A) is shown. In FIG. 9A, the first component 300 is secured relative to the second component via interaction of the outwardly deflected inwardly deflected element and the shoulder of the engagement element 210 (e.g., as depicted and described above with regard to FIG. 8C).

Advancement of the tool over the second component (e.g., as depicted and described above with regard to FIG. 2) causes the tapered portion 415 of the disengagement element 410 to inwardly deflect the inwardly deflecting element of the first component 300, disengaging the inwardly deflecting element from the groove of the engagement element 410 (FIG. 9B). As shown in FIG. 9B, the retention portion 417 of the disengagement element 410 causes sufficient inward deflection of the inwardly deflectable element to disengage the deflectable element form the engagement element 201, allowing withdrawal of the second element over the first element 300. Further advancement of the tool over the first and second components is prevented by interaction of the disengagement element 410 and the bottom flange 320 of the first component.

Figure 10:
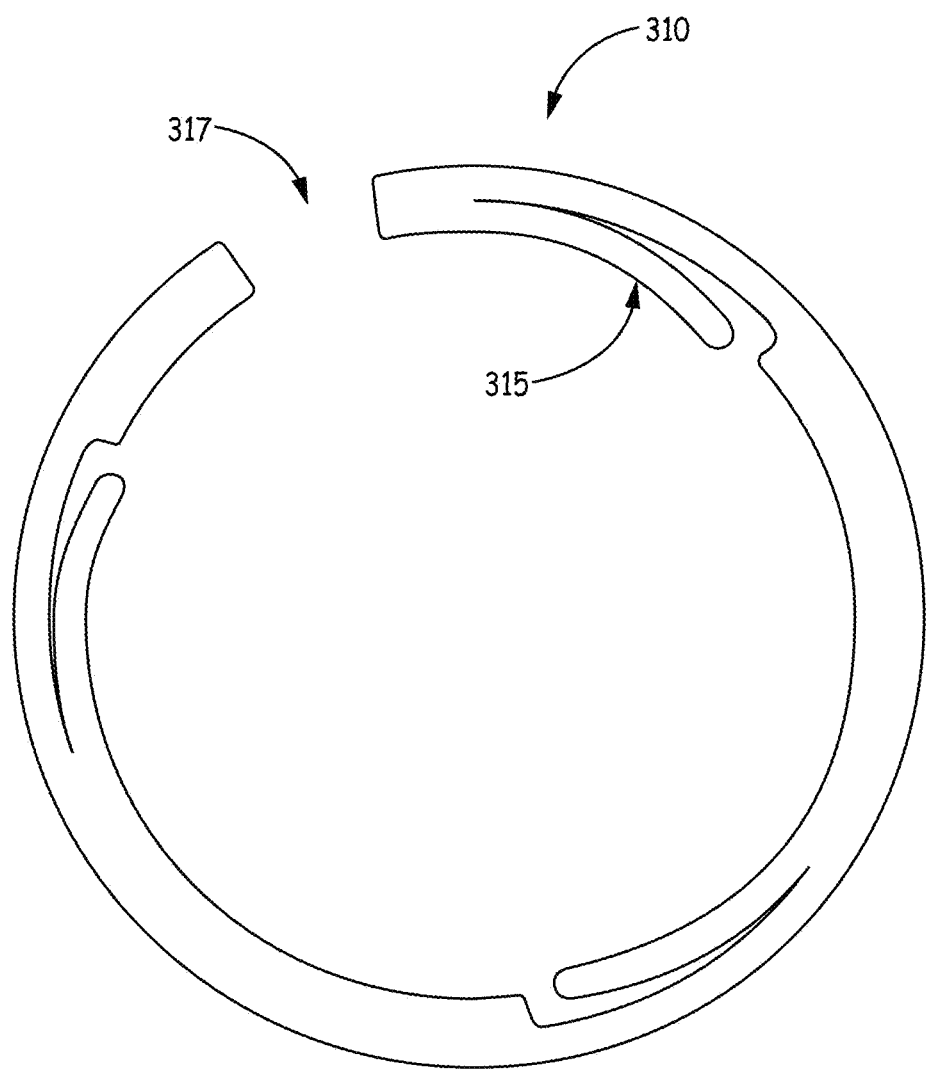
FIG. 10 is a schematic drawing of a top view of an embodiment of an inwardly deflectable element.

Referring now to FIG. 10, a schematic top view of an embodiment of an inwardly deflectable element 310 is shown. The element 310 includes a plurality of outwardly biasing elements 315. The biasing elements 315 may interact with an inner wall of a recess of the first component (such as inner wall 335 of recess 330 depicted in FIG. 3) to outwardly bias the deflectable element 310. The depicted deflectable element 310 includes a slit or open region 317 to facilitate insertion of the element 310 into the recess of the first component.

Figure 11:
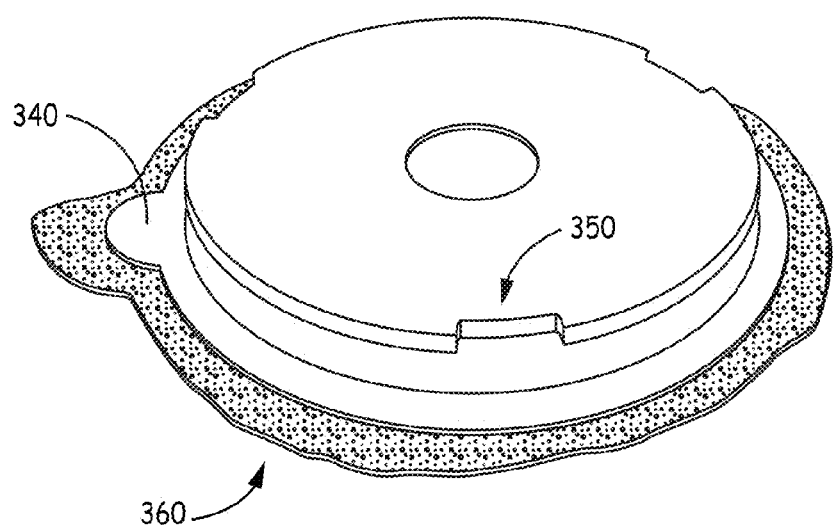
FIG. 11 is a schematic drawing of a perspective view of an embodiment of a component of a multicomponent infusion device assembly.
Figure 12:
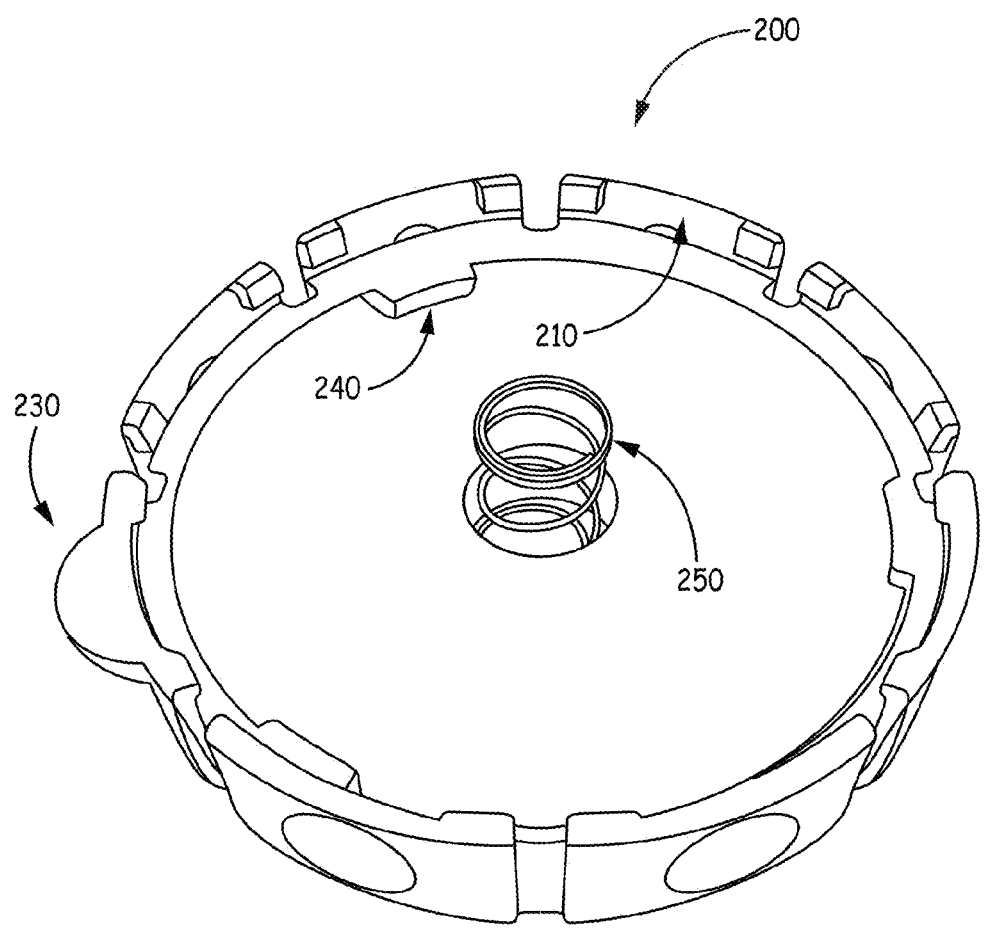
FIG. 12 is a schematic drawing of a perspective view of an embodiment of a component of a multicomponent infusion device assembly.

Referring now to FIG. 11, a schematic perspective view of an embodiment of a first component of a multicomponent infusion device assembly is shown. The depicted first component includes an external tab 340 to serve as an alignment indicator with a corresponding external tab of a second component (e.g., as shown in FIG. 12). The depicted first component also includes alignment features 350, such as indents, to align the first component with corresponding complementary features of the second component (e.g., as shown in FIG. 12). It will be understood that the first component may have any suitable number of alignment indicators or features, which each individually may be of any suitable size or shape. The depicted first component also includes a release liner 360 and adhesive (not shown) between the release liner 360 and the bottom flange of the first component. The release liner 360 may be removed to expose the adhesive so that the first component may be adhered to skin of a patient.

Referring now to FIG. 12, a schematic perspective view showing a bottom of an embodiment of a second component 200 of a multicomponent infusion device assembly is shown. As indicated above, the second component 200 may optionally include an external alignment tab and alignment features 240, such as detents, complementary to alignment features of the first component. It will be understood that the second component may have any suitable number of alignment indicators or features, which may each individually be of any suitable shape or size. The depicted second component includes a spring element 250 to bias the second component away from the first component. Such a spring element may facilitate disengagement of the first and second components.

Figure 13:
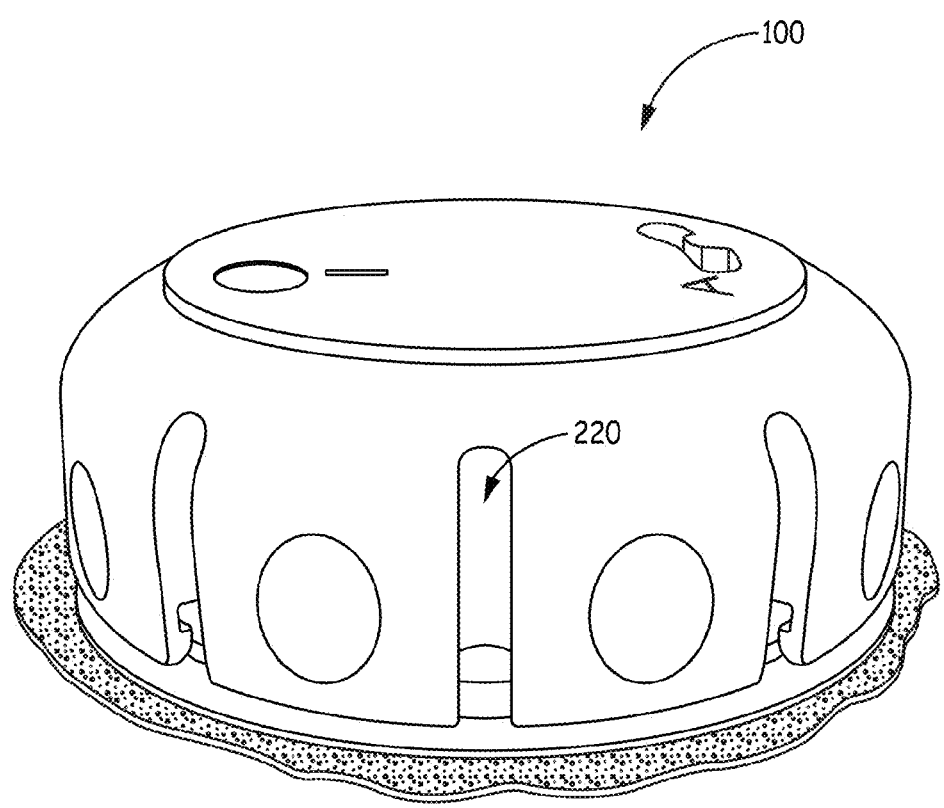
FIG. 13 is a schematic drawing of a perspective view showing the component of FIG. 11 secured or locked relative to the component of FIG. 12.

Referring now to FIG. 13, a schematic perspective view is shown of an embodiment of an assembled infusion device assembly 100 in which the first component of FIG. 11 is secured or locked relative to the second component of FIG. 12. The second component includes channels 220 in the housing for receiving and guiding a disengagement element of a disengagement tool.

Figure 14:
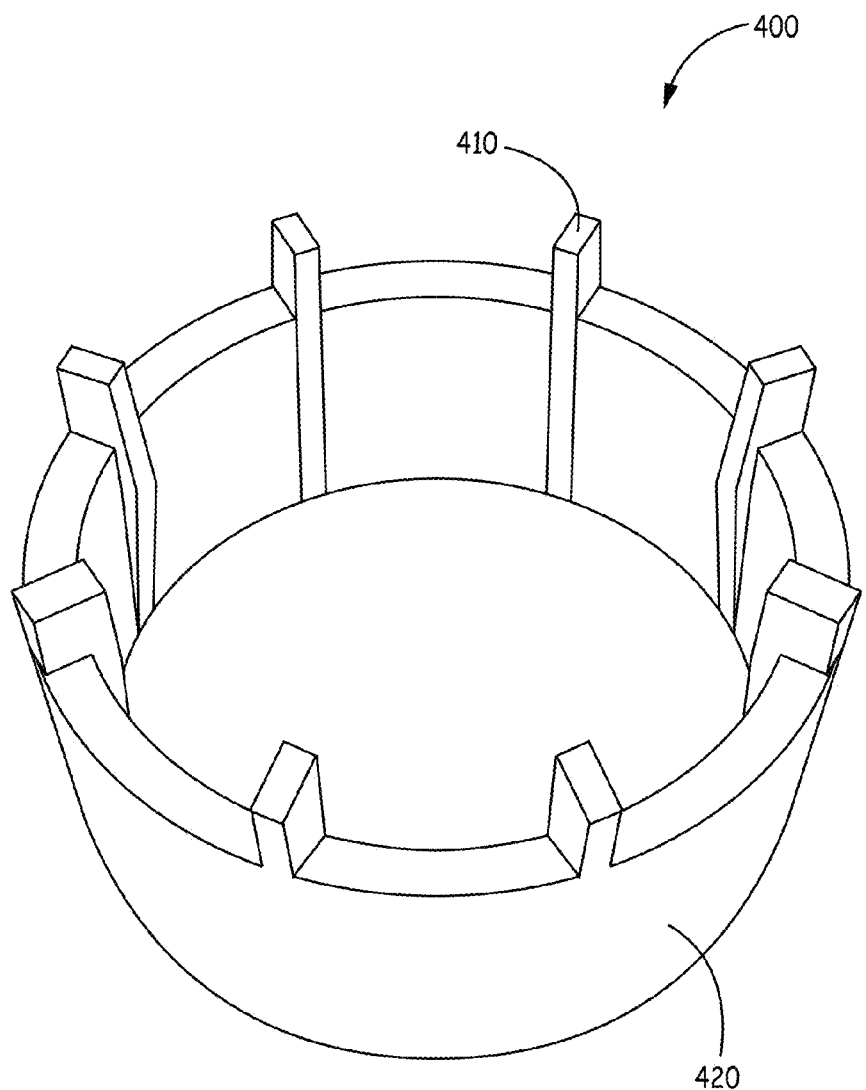
FIG. 14 is a schematic drawing of a perspective view of an embodiment of a disengagement tool.

Referring now to FIG. 14, a schematic perspective view of an embodiment of a disengagement tool 400 is shown. The depicted disengagement tool 400 includes disengagement elements 410 extending from a generally tubular body 420 that forms a lumen of sufficiently large inner diameter to allow the tool to be advanced over the second component of the infusion device assembly.

Figure 15:
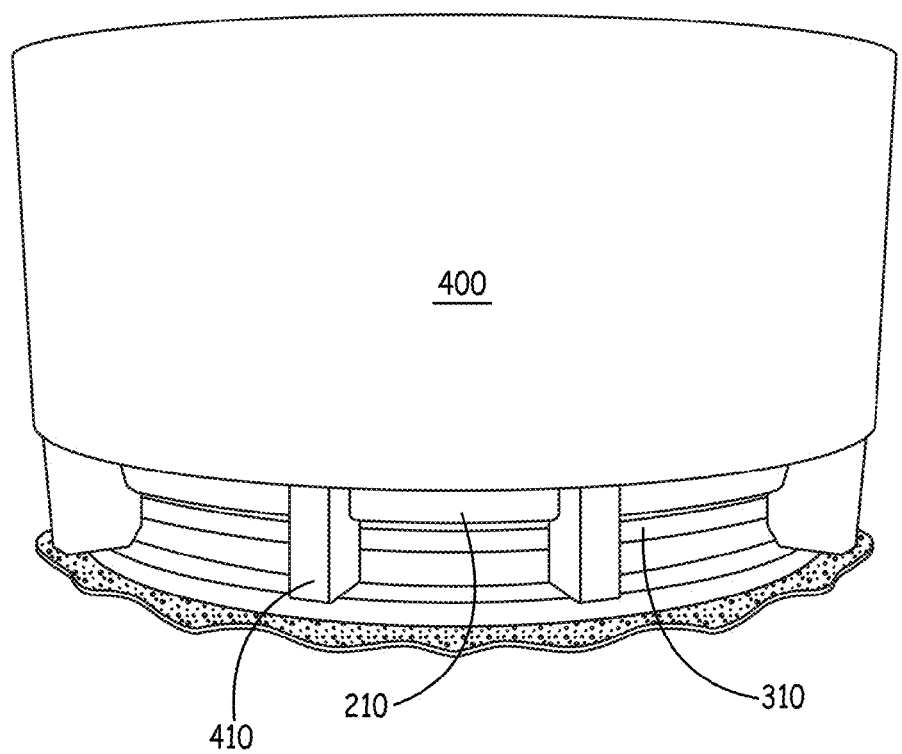
FIG. 15 is a schematic drawing of a perspective view of the tool of FIG. 14 interacting with the components shown in FIG. 13.

Referring now to FIG. 15, a schematic perspective view is shown in which the tool 400 of FIG. 14 is interacting with the components of the device assembly of FIG. 13 to disengage the first component from the second component. Disengagement elements 410 of the tool 400 maintain the inwardly deflectable element 310 in an inwardly deflected orientation such that the engagement elements 210 of the second component may be released and the second component may be withdrawn from the first component as depicted.

Figure 16:
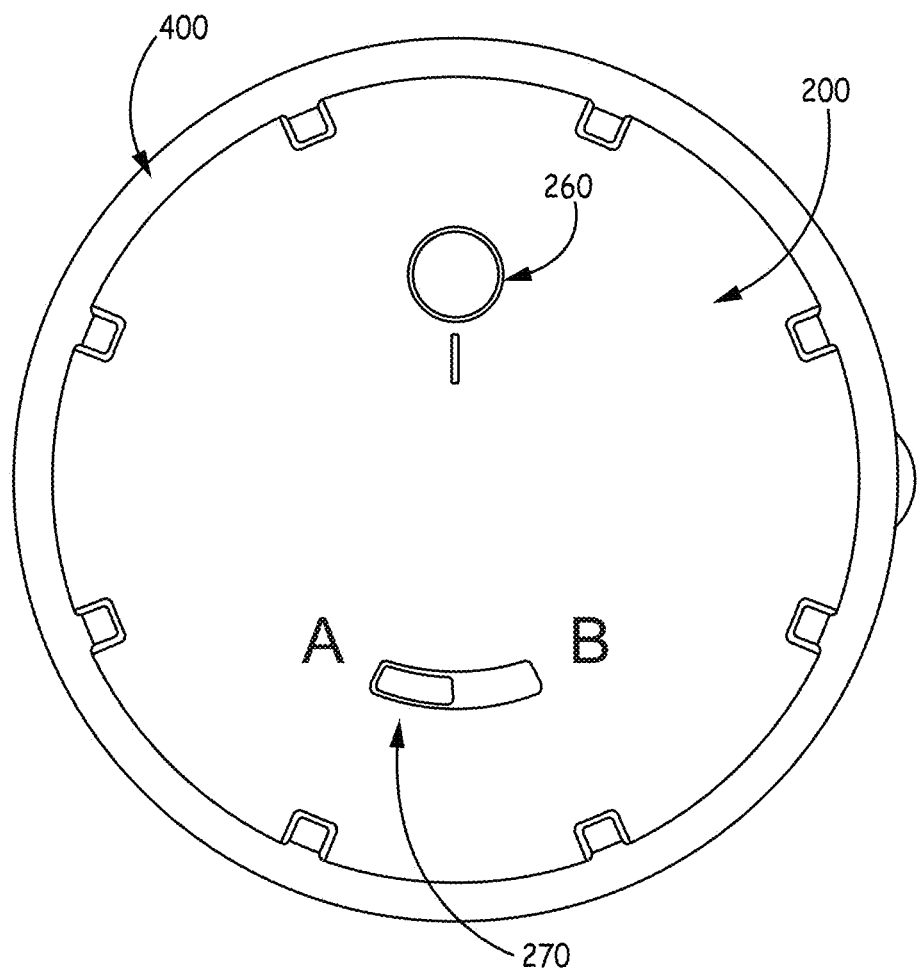
FIG. 16 is a schematic drawing of a top view of an embodiment of a disengagement tool disposed over an embodiment of a multicomponent infusion device assembly.

Referring now to FIG. 16, a schematic drawing of a top view of an embodiment of a disengagement tool 400 disposed over an embodiment of a multicomponent infusion device assembly is shown. In the top view, only the second component 200 of the infusion device assembly is visible. The top of the depicted second component includes a pump mechanism control element 270, such as a switch, to control the rate at which a pump mechanism housed in the second component delivers therapeutic agent from a reservoir housed in the first component. The depicted second component also includes an indicator 260, such as an LED, to alert a user of the device assembly of one or more conditions associated with the device, such as clogged or occluded flow, low reservoir, stale therapeutic agent, or any other condition for which is may be desirable to alert the user.

Figure 17:
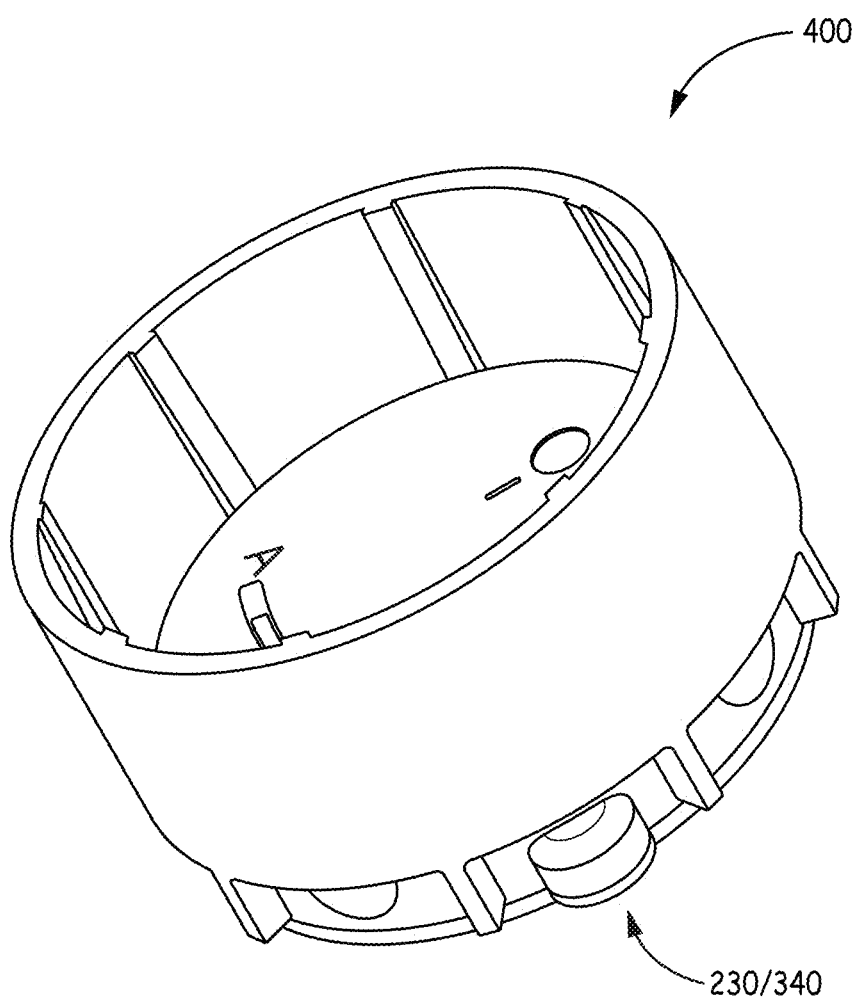
FIG. 17 is a schematic drawing of a perspective view of an embodiment of a disengagement tool disposed over an embodiment of a multicomponent infusion device assembly.

Referring now to FIG. 17, a schematic drawing is shown of a perspective view of an embodiment of a disengagement tool 400 disposed over an embodiment of a multicomponent infusion device assembly. The first device assembly component includes an alignment tab 340, and the second device assembly component includes a complementary alignment tab 230.

Figure 18:
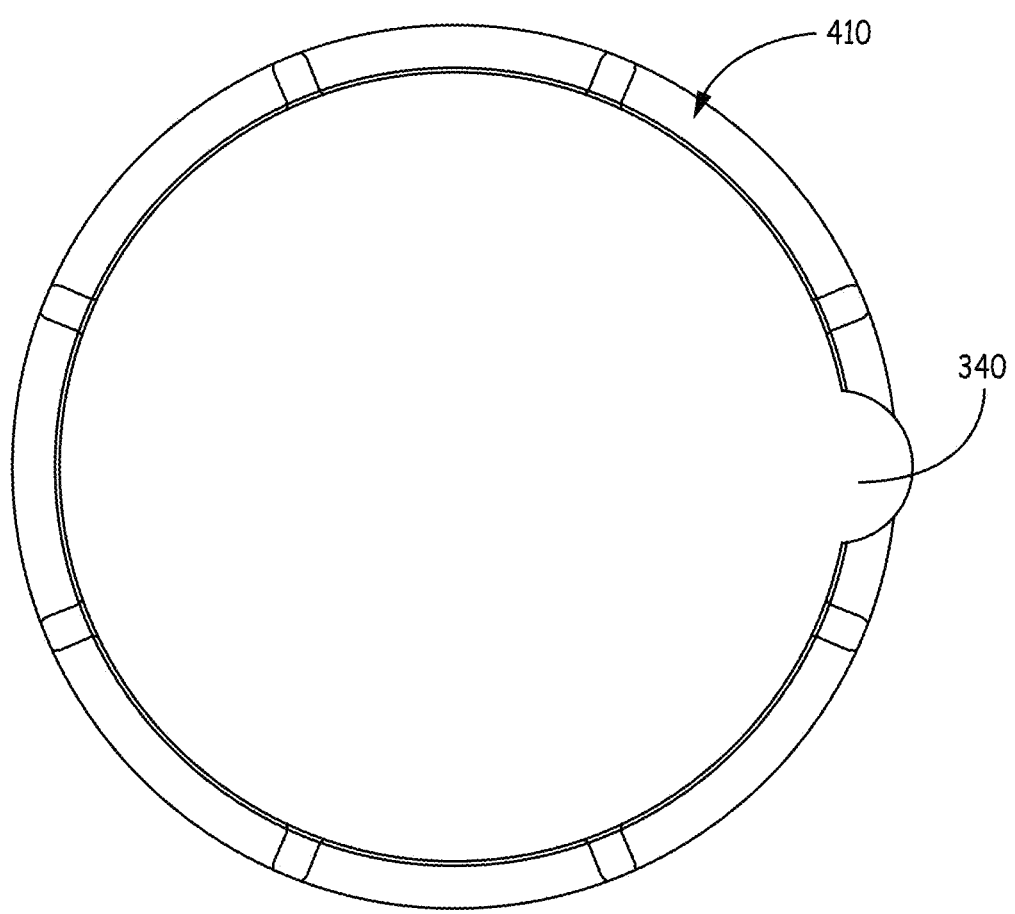
FIG. 18 is a schematic drawing of a bottom view of an embodiment of a disengagement tool disposed over an embodiment of a multicomponent infusion device assembly.

Referring now to FIG. 18, a schematic drawing is shown of a bottom view of an embodiment of a disengagement tool disposed over an embodiment of a multicomponent infusion device assembly. Disengagement elements 410 and external alignment tab 340 of the first component of the infusion device assembly are shown.

While the pump-containing component is shown as being the second component in some of the figures presented herein and the reservoir-containing component is shown as being the first component in some of the figures presented herein, it will be understood that the pump-containing component may be the first component and the reservoir-containing component may be the second component.

While the disengagement tool is depicted as a separate element in some of the figures presented herein, it will be understood that the disengagement component may be integrated into the second component. For example, an integrated disengagement component may be actuated by a push button mechanism (not shown) or any other suitable mechanism depending on how the disengagement component is integrated with the second component.

A number of previously described wearable infusion devices or device assemblies may be modified in accordance with the teachings herein. Examples of such devices or assemblies that may be readily modified in accordance with the teachings presented herein include those shown and described in U.S. Pat. Nos. 4,562,751; 4,678,408; 4,685,903; 5,080,653; 5,097,122, and 6,551,276, which are each hereby incorporated herein by reference in their respective entireties to the extent that they do not conflict with the disclosure presented herein.

Thus, embodiments of INFUSION DEVICE ASSEMBLY are disclosed. One skilled in the art will appreciate that the articles, systems and methods described herein can be practiced with embodiments other than those disclosed. The disclosed embodiments are presented for purposes of illustration and not limitation.

What is claimed is:

1. A wearable infusion device assembly comprising:
   a first component forming a first portion of a housing of the assembly and comprising an inwardly deflectable element; and
   a second component forming a second portion of the housing of the assembly and comprising a plurality of engagement elements, wherein each engagement element of the plurality of engagement elements comprises (i) a tapered portion configured to cause the inwardly deflectable element of the first component to deflect inwardly as the second component is advanced about the first component and (ii) a shoulder proximal to the tapered portion,
   wherein the inwardly deflectable element of the first component is configured to deflect outwardly after the shoulders pass the inwardly deflectable element as the second component is advanced about the first component,
   wherein the shoulder and the inwardly deflectable element are configured to cooperate to prevent withdrawal of the second component over the first component after the inwardly deflectable element of the first component has deflected outwardly after the shoulders have passed the inwardly deflectable element as the second component is advanced about the first component,
   wherein the second portion of the housing defines at least one channel positioned between two engagement elements of the plurality of engagement elements, wherein the at least one channel is configured to provide access to the inwardly deflectable element; and
   further comprising a disengagement component configured to advance over the second component towards the first component, the disengagement component having a disengagement element comprising a tapered portion configured to cause the inwardly deflectable element of the first component to deflect inwardly as the disengagement component is advanced about the first component,
      wherein the tapered portion of the disengagement element is configured to sufficiently inwardly deflect the inwardly deflectable element to allow the second component to be withdrawn over the first component.

2. A wearable infusion device assembly according to claim 1, wherein the disengagement element further comprises a retention portion proximal to the tapered portion, wherein the retention portion is configured to retain the inwardly deflectable element in the sufficiently inwardly deflected position.

3. A wearable infusion device assembly according to claim 1, wherein the at least one channel is configured to receive the disengagement element as the disengagement component is advanced over the second component towards the first component.

4. A wearable infusion device assembly according to claim 1, wherein the disengagement component comprises a plurality of disengagement elements.

5. A system comprising:
   (i) a wearable infusion device assembly comprising:
      a first component forming a first portion of a housing of the assembly and comprising an inwardly deflectable element; and
      a second component forming a second portion of the housing of the assembly and comprising a plurality of engagement elements, wherein each engagement element of the plurality of engagement elements comprises (i) a tapered portion configured to cause the inwardly deflectable element of the first component to deflect inwardly as the second component is advanced about the first component and (ii) a shoulder proximal to the tapered portion,
      wherein the inwardly deflectable element of the first component is configured to deflect outwardly after the shoulders pass the inwardly deflectable element as the second component is advanced about the first component,
      wherein the shoulder and the inwardly deflectable element are configured to cooperate to prevent withdrawal of the second component over the first component after the inwardly deflectable element of the first component has deflected outwardly after the shoulders have passed the inwardly deflectable element as the second component is advanced about the first component,
      wherein the second portion of the housing defines at least one channel positioned between two engagement elements of the plurality of engagement elements, wherein the at least one channel is configured to provide access to the inwardly deflectable element; and
   (ii) a disengagement tool configured to advance over the second component towards the first component, the disengagement tool having a disengagement element comprising a tapered portion configured to cause the inwardly deflectable element of the first component to deflect inwardly as the disengagement tool is advanced about the first component,
      wherein the tapered portion of the disengagement tool is configured to sufficiently inwardly deflect the inwardly deflectable element to allow the second component to be withdrawn over the first component.

6. A system according to claim 5, wherein the disengagement element further comprises a retention portion proximal to the tapered portion, wherein the retention portion is configured to retain the inwardly deflectable element in the sufficiently inwardly deflected position.

7. A system according to claim 5, wherein the at least one channel is configured to receive the disengagement element as the disengagement tool is advanced over the second component towards the first component.

8. A system according to claim 5, wherein the disengagement tool comprises a plurality of disengagement elements.

\* \* \* \* \*